US00PP10821P

United States Patent [19]

Olesen et al.

[11] Patent Number: Plant 10,821

[45] Date of Patent: Mar. 9, 1999

[54] FLORIBUNDA ROSE PLANT NAMED 'POULELAP'

[75] Inventors: L. Pernille Olesen; Mogens N. Olesen, both of Fredensborg, Denmark

[73] Assignee: Poulsen Roser ApS, Fredensborg, Denmark

[21] Appl. No.: 865,463

[22] Filed: May 29, 1997

[51] Int. Cl.[6] ..... A01H 5/00

[52] U.S. Cl. ..... Plt./26

[58] Field of Search ..... Plt./22, 23, 24, Plt./26

[56] References Cited

PUBLICATIONS

UPOV–ROM, 1997/Apr., Plant Variety Database, GTI Jouve Retrieval Software, citation for 'POOLelap'.

*Primary Examiner*—Howard J. Locker

[57] ABSTRACT

A new soft pink floribunda rose plant which has abundant flowers, dark green glossy foliage, compact even growth, and rapid repeat flowering. The variety successfully propagates from softwood cuttings and is suitable for year round production in commercial glasshouses and nurseries. This new and distinct variety has shown to be uniform and stable in the resulting generations from such asexual propagation.

2 Drawing Sheets

SUMMARY OF THE INVENTION

The present invention constitutes a new and distinct variety of a floribunda rose plant which originated from a controlled crossing between 'MACrexy' × an unnamed seedling. The new rose may be distinguished from its seed parent by the following combination of characteristics: 'MACrexy' is a clear pink floribunda rose described under U.S. Plant Pat. No. 6,713. The new rose has superior disease resistance to mildew and rust in outdoor culture. The new rose may be distinguished from its pollen parent by the following combination of characteristics: The unnamed seedling is a compact floribunda with flower color of Red Group 56B. The two parents were crossed during the summer of 1989 and the resulting seed was planted in December 1989 in a controlled environment. The new variety is named 'POULelap'.

The objective of the hybridization of this rose variety for commercial greenhouse culture was to create a new and distinct variety with:

1. Uniform and abundant flowers with good repeat bloom;

2. Attractive long lasting foliage and uniform compact growth,

3. Year-round flowering under glasshouse and nursery conditions;

4. Suitability for production from softwood cuttings in pots; and

5. Durable flowers and foliage which make a variety suitable for distribution in the floral and nursery industry.

This combination of qualities was not present in previously available commercial cultivars of this type and distinguish 'POULelap' from all other varieties of which we are aware.

The seeds from the hybridization were germinated and evaluations were conducted of the resulting rose plants in a controlled environment.

'POULelap' was selected by L. Pernille and Mogens N. Olesen in their rose development program in Fredensborg, Denmark in June, 1990.

Asexual reproduction of 'POULelap' by cuttings and traditional budding was first done by L. Pernille and Mogens N. Olesen in August, 1990. This initial and subsequent propagations have demonstrated that the characteristics of 'POULelap' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers, leaves, stems, and a plant of 'POULelap'.

Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting Prickles; and

6. Leaves.

Specifically illustrated in SHEET 2 are flower buds and blooms in greater detail.

DETAILED DESCRIPTION OF THE VARIETY

The following is a detailed description of 'POULelap', as observed in its growth in glasshouses in Fredensborg, Denmark and Half Moon Bay, Calif., and in field nursery in Applegate, Oreg. Descriptions were made from plants treated with growth regulators normally used in the greenhouse production process. The growth regulator Paclobutrazol was applied at 30 ppm weekly for three weeks beginning at a plant age of 10 weeks. The peduncle lengths mentioned may actually be shorter and the foliage color several shades darker than on untreated specimens. Color references are made using The Royal Horticultural Society (London, England) Colour Chart, 1995.

For a comparison, the nearest existing rose variety is POULrek, a patented variety described and illustrated in U.S. Plant Pat. No. 9,688 and issued on Nov. 12, 1996. Chart 1 details several physical characteristics of 'POULelap' and the comparison variety.

CHART 1

| | 'POULelap' | 'POULrek' |
|---|---|---|
| Upper side of petal surface | RHS 27 D of the Orange Color Group | RHS 36 D of the Red Color Group |

CHART 1-continued

| | 'POULelap' | 'POULrek' |
|---|---|---|
| Reverse side of petal surface | RHS 19 D of the Yellow-Orange Color Group | RHS 36 D of the Red Color Group |

Parents: 'MACrexy' × unnamed seedling.
Classification:
*Botanical.*—Rosa hybrida.
*Commercial.*—Floribunda.

Flower and flower bud

Blooming cycle: Recurrent.
Flower bud:
*Size.*—20–22 mm in length when petals are just beginning to crack open.
*Bud form.*—Pointed to ovoid.
*Bud color.*—Under high light conditions, bud has Greyed-Red 179A blush as the sepals part. R.H.S. 27 D of the Orange Color Group at ¼ opening.
*Sepals.*—R.H.S. 143 C of the Green Group. Foliaceous appendages lacking. Surfaces of sepals with light pubescence. Stipitate glands present on outer surface.
*Peduncle.*—Surface: Smooth, with stipitate glands present. Length: 25–35 mm average length. Color: R.H.S. 143 C of the Green Group. Princkles: None.
*Receptacle.*—Surface: Smooth, Glabrous. Shape: Funnel to urn shaped. Size: Small to medium. 7 mm×8 mm. Color: R.H.S. 143 C of the Green Color Group.
*Borne.*—On greenhouse plants, one to four buds per flowering stem. On plants growing outdoors, eight to fifteen buds per flowering stem.
Flower bloom:
*Diameter.*—Medium. 60–70 mm on average.
*Form.*—Upon opening, pointed to ovoid. Completely open form is flattened convex with petals reflexing somewhat.
*Petalage.*—Double average range: 20–25 petals. Petaloids not generally present.
*Color.*—Upon opening, the upper surface is R.H.S. 27 D of the Orange Color Group. Upon opening, the reverse side is R.H.S. 19 D of the Yellow-Orange Color Group. After opening, the upper surface is R.H.S. 27 D of the Orange Color Group. After opening, the reverse surface is R.H.S. 19 D of the Yellow-Orange Color Group. A small petal spot R.H.S. 4 C of the Yellow Color Group exists on the inner side of the petal base. A small petal spot R.H.S. 4 D of the Yellow Color Group exists on the outer side of the petal base.
*Reflex.*—Petals reflex backwards slightly.
*Variations.*—None.
*Fragrance.*—None to light.
*Duration.*—Quick cycle. Repeat bloomer. 8–11 days as a cut flower and 10–14 days on the plant.
Reproductive organs:
*Pollen.*—Golden yellow. Average abundance.
*Anthers.*—Size: Small. Color: Golden-yellow.
*Filaments.*—Color: Yellow to Yellow-white.
*Stigmas.*—Located at same position as anthers.
*Styles.*—Color: Yellow-white.

Plant

Plant growth: Vigorous, evenly compact and bushy. When grown as a 15 cm pot plant, the average height of the plant itself is 25–30 cm and the average width is 20–25 cm. When grown as a nursery plant on its own roots the average plant height is 50–60 cm and the average plant width is 50–60 cm.
Stems:
*Color.*—Young wood: Light green. R.H.S. 138 B of the Green Color Group. Older wood: R.H.S. 138 A of the Green Color Group.
*Prickles.*—Incidence: Moderate. Size: Average length: 6–7 mm. Color: Red Group 48D. Shape: Linear to concave.
*Bark.*—Young wood: Smooth. Older wood: Smooth.
*Stem length.*—Flowering stems 25–35 cm.
Plant foliage:
*Normal number of leaflets on average leaves.*—5 leaflets, some with 7 leaflets, the inner most being reduced in size.
*Leaf size.*—Medium sized. 55×65 mm.
*Abundance.*—Above average abundance.
*Color.*—Mature foliage: Upper leaf surface: Dark green, glossy. Between R.H.S. 137 A and R.H.S. 139 A of the Green Group. Lower leaf surface: Medium green. R.H.S. 138 B of the Green Color Group. Juvenile foliage: Green. Group 139C with red intonation of 179B.
Plant leaves and leaflets:
*Stipules.*—Present. Average length 10 mm. Tips angle at 45° or nearly so. Stipitate glands present on margins. Juvenile stipules colored Green Group 139C with red intonation of Greyed-Red Group 179B.
*Petiole.*—Length: 20 mm, shorter on those leaves with 7 leaflets. Underneath: With prickles.
*Rachis.*—Green Group 139C.
*Edge.*—Smooth with stipitate glands at intervals.
*Shape.*—Leaflets are ovate to round.
*Leaflets.*—Number: 5.
*Other.*—Semi-glossy to glossy. Thick texture.
Disease resistance: Above average resistance to mildew, rust, and black spot under normal growing conditions in Half Moon Bay, Calif. and Fredensborg, Denmark.

We claim:

1. A new and distinct variety of rose plant of the floribunda class, substantially as herein illustrated and described, as a distinct and novel rose variety due to its abundant soft pink flowers, dark green glossy foliage, compact even growth, and rapid repeat flowering suitable for production from softwood cuttings in pots and traditional budding with durable flowers and foliage making the variety suitable for distribution in the floral and nursery industry.

* * * * *

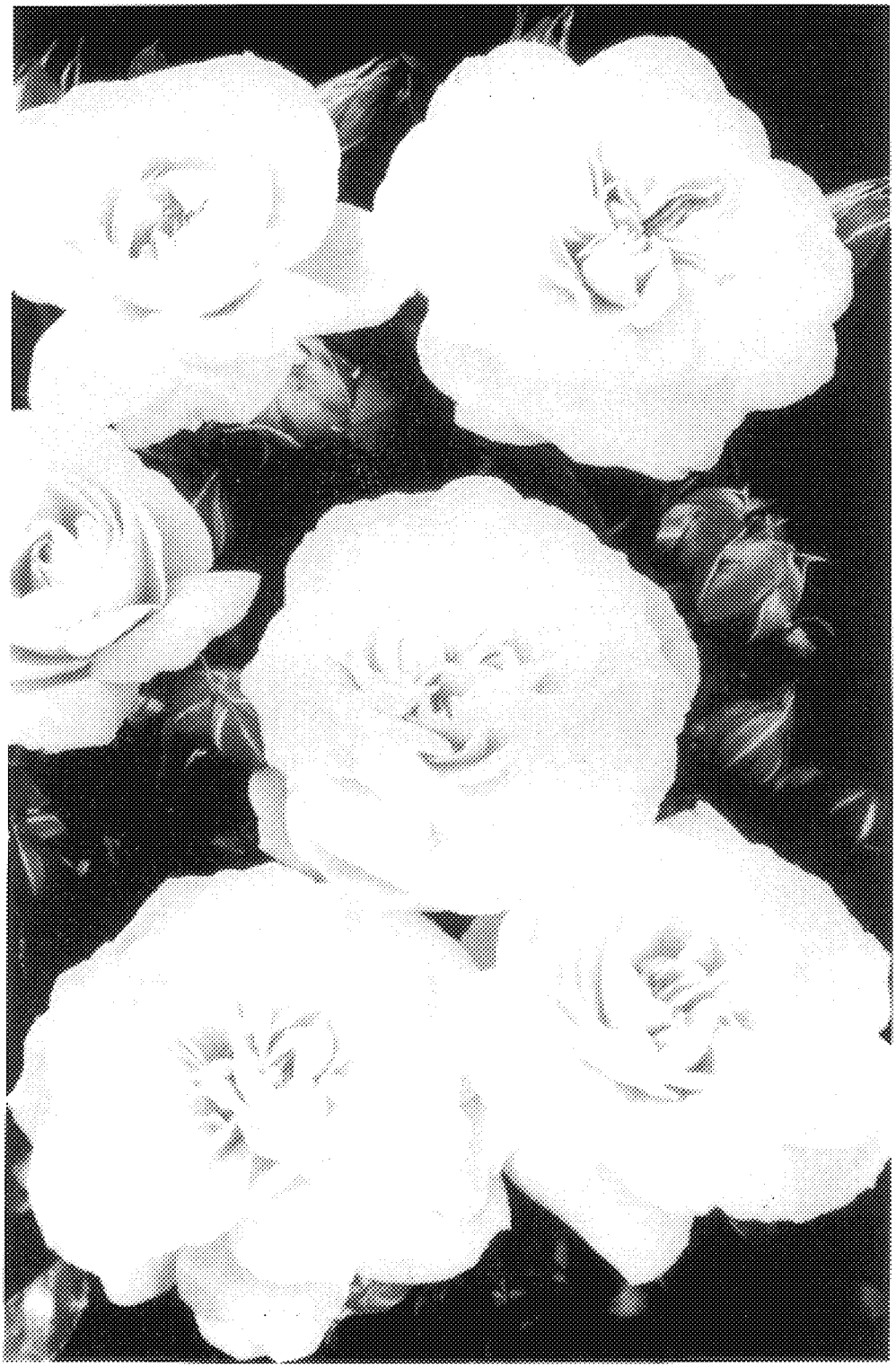

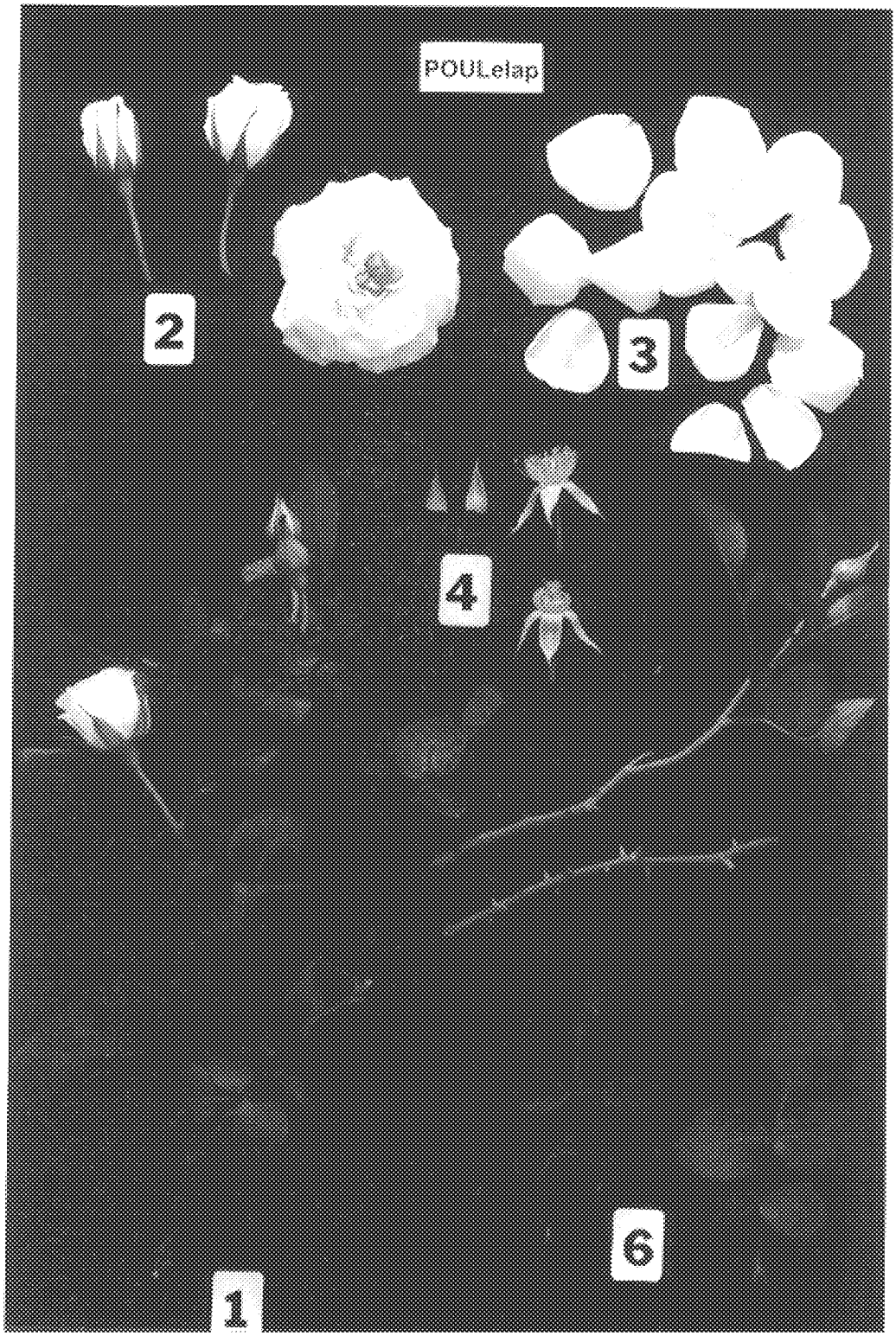
POULelap
2
3
4
6
1